United States Patent
Regensburger et al.

(10) Patent No.: US 11,801,069 B1
(45) Date of Patent: Oct. 31, 2023

(54) DEVICE AND METHOD FOR ORIENTING A MEDICAL OBJECT

(71) Applicant: Siemens Healthcare GmbH, Erlangen (DE)

(72) Inventors: ALois Regensburger, Poxdorf (DE); Oliver Hornung, Unterleinleiter (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 18/142,772

(22) Filed: May 3, 2023

(30) Foreign Application Priority Data

May 17, 2022 (DE) ..................... 10 2022 204 859.8

(51) Int. Cl.
*A61B 17/34* (2006.01)
*A61B 90/00* (2016.01)

(52) U.S. Cl.
CPC .......... *A61B 17/3403* (2013.01); *A61B 90/39* (2016.02); *A61B 2017/3405* (2013.01); *A61B 2090/3937* (2016.02)

(58) Field of Classification Search
CPC ............ A61B 34/20; A61B 2034/2046; A61B 2034/2055; A61B 2034/2051; A61B 90/50; A61B 90/13; A61B 90/11; A61B 90/10; A61B 2090/101; A61B 17/3403; A61B 90/39; A61B 2017/3405; A61B 2090/3937
See application file for complete search history.

(56) References Cited

U.S. PATENT DOCUMENTS

| | | | |
|---|---|---|---|
| 5,766,126 | A | 6/1998 | Anderson |
| 5,810,841 | A | 9/1998 | Mcneirney |
| 5,957,933 | A | 9/1999 | Yanof et al. |
| 2016/0206383 | A1 | 7/2016 | Leong et al. |

(Continued)

FOREIGN PATENT DOCUMENTS

| | | |
|---|---|---|
| DE | 69620521 T2 | 5/2002 |
| DE | 69829161 T2 | 4/2005 |
| DE | 69728908 T2 | 6/2005 |

(Continued)

OTHER PUBLICATIONS

Arnolli, Maarten Menno. "Development of a precision system for image-guided needle placement: from scratch to clinic." (2017). pp. 1-222.

*Primary Examiner* — Katherine M Shi
(74) *Attorney, Agent, or Firm* — Lempia Summerfield Katz LLC (57) ABSTRACT

A device for orienting a medical object in respect of an object under examination includes an orientation element, a guide element, an ancillary element, and a light guiding device. The orientation element is movably mounted about a center of rotation and is configured for the longitudinal guidance of the medical object along a guide axis. The ancillary element includes an identification marker configured to be arranged in the center of rotation. The light guiding device is configured to emit a predefined distribution of light for specification of a path. The arrangement of orientation element and ancillary element may be moved about the center of rotation arranged on the path, such that the predefined distribution of light illuminates the identification marker with a predefined light pattern, when the guide axis of the orientation element is oriented in a defined positional relationship in respect of the path.

16 Claims, 7 Drawing Sheets

(56) References Cited

U.S. PATENT DOCUMENTS

2019/0269470 A1  9/2019  Barbagli et al.
2020/0085527 A1  3/2020  Alzaga et al.

FOREIGN PATENT DOCUMENTS

DEVICE AND METHOD FOR ORIENTING A MEDICAL OBJECT

The present patent document claims the benefit of German Patent Application No. 10 2022 204 859.8, filed May 17, 2022, which is hereby incorporated by reference in its entirety.

TECHNICAL FIELD

The disclosure relates to a device for orienting a medical object in respect of an object under examination, a system, and a method for orienting a medical object.

BACKGROUND

To orient medical objects, (e.g., a needle), use is frequently made of what are known as needle sleeve holders, which mechanically stably orient a hollow cylinder, through which the medical object, in particular the needle, may be pushed. As a result, a planned path for the medical object, in particular the needle, may be specified precisely, in particular with greater accuracy than in the case of freehand orientation of the medical object. For orientation of the sleeve, use may be made of visual navigation or a robot. For example, by a laser an injection site for the medical object, in particular the needle, on the object under examination may be specified. After a tip of the medical object has been positioned, in particular manually, on the injection site specified by the laser a proximal section of the medical object may be repositioned, in particular manually, such that the proximal section too is arranged on a path specified by the laser. A disadvantage of this method for orientating the medical object is that it is frequently imprecise, painful, and may result in increased blood loss on the part of the object under examination.

Furthermore, various orientation aids exist which may enable a more intuitive orientation of the sleeve in respect of the reader, in that the orientation aid is attached to the sleeve and/or is introduced into the sleeve in place of the medical object. Despite the use of an orientation aid the orientation of the sleeve may be time-consuming and complex because of the many degrees of spatial freedom.

SUMMARY AND DESCRIPTION

It is hence the object of the present disclosure to enable a time-efficient, precise, and intuitive orientation of a medical object in a defined positional relationship in respect of a specified path.

The scope of the present disclosure is defined solely by the appended claims and is not affected to any degree by the statements within this summary. The present embodiments may obviate one or more of the drawbacks or limitations in the related art.

The first aspect of the disclosure relates to a device for orienting a medical object in respect of an object under examination. The medical object includes an orientation element, a guide element, an ancillary element, and a light guiding device. The orientation element is movably mounted so as to be forcibly guided by the guide element about a center of rotation, it being possible for the center of rotation to be repositioned by repositioning the guide element. The orientation element is configured for the longitudinal guidance of the medical object along a guide axis specified by the orientation element. Further, the ancillary element has an identification marker. The ancillary element may be arranged in a defined arrangement in respect of the orientation element, such that the identification marker is arranged in the center of rotation. The light guiding device is configured to emit a predefined distribution of light which specifies a path. The predefined distribution of light illuminates the identification marker when the center of rotation is arranged on the path at a distance from the object under examination. In this case, the arrangement of orientation element and ancillary element about the center of rotation arranged on the path in an operating state of the device may be movable, such that the predefined distribution of light illuminates the identification marker with a predefined light pattern, if the guide axis of the orientation element is oriented in a defined positional relationship in respect of the path.

The medical object may be a surgical instrument, (e.g., a needle such as a puncture needle, or a drill), a diagnostic instrument, (e.g., an endoscope such as a laparoscope), a catheter, or a combination thereof. The medical object may advantageously be configured at least partially, in particular completely, to be rigid and elongated, in particular rod-shaped and/or needle-shaped.

The object under examination may be a male or female human or animal patient and/or an examination phantom.

The orientation element may be configured to guide the medical object along the guide axis, in particular on the guide axis. In particular, the orientation element may be configured to restrict degrees of freedom of movement of the medical object to a translational motion along the guide axis and a rotation about the guide axis. For this, the orientation element may be configured to receive the medical object at least partially and to guide the medical object along the guide axis thanks to an interaction, (e.g., mechanical and/or electromagnetic interaction), between the orientation element and the medical object. The guide axis may in this case be specified as stationary in respect of the orientation element, for example, thanks to a geometry of the orientation element.

The guide element may advantageously be configured to restrict degrees of freedom of movement of the orientation element to a rotation about the center of rotation. The guide element may include a holding device, (e.g., a stand and/or a robot arm), on which the orientation element is mounted so as to be movable about the center of rotation. In this case, the center of rotation may be specified by the guide element, in particular a geometry of the guide element. The center of rotation may be repositionable, in particular translatable, by repositioning the guide element, in particular a translational motion of at least one part of the guide element. In this case, the guide element may be configured to be repositioned manually, for example, by an application of force by a medical operative, and/or in a motorized manner, for example, by a motor drive. The orientation element may be attached to the guide element, wherein the orientation element may be mounted so as to be movable, in particular rotatable, about the center of rotation by a movement of at least one part of the guide element. The guide element may further be configured to specify a radius of the movement, in particular the rotation, of the orientation element about the center of rotation.

The center of rotation may describe a spatial position about which the orientation element may be moved in a forcibly guided manner by the guide element, in particular rotated. In this case, the center of rotation may be arranged on the orientation element or at a distance from the orientation element.

The ancillary element has the identification marker. In this case, the identification marker may be configured as a graphical marking, for example, a graphical object and/or a pattern, on a surface of the ancillary object. Alternatively, or additionally, the identification marker may be configured as a structural element, for example, a recess, in particular a slot, and/or an elevation, of the ancillary element. The identification marker may include a first subsidiary identification marker and a second subsidiary identification marker. In this case, the first subsidiary identification marker may mark a point on the ancillary element, which is to be arranged in the center of rotation. The first and the second subsidiary identification markers may have a defined, in particular unchanging, arrangement in respect of one another, in particular a relative positioning. The arrangement of the first and second subsidiary identification markers may define a longitudinal axis of the ancillary element which is to be arranged on the specified path. In this case, the identification marker, in particular the first and the second subsidiary identification marker, may be configured, when the longitudinal axis of the ancillary element is arranged on the path, to be illuminated with the predefined light pattern. The first and the second subsidiary identification marker may be configured to be at a distance from one another and/or at least to be partially contiguous. Further, the first and the second subsidiary identification marker may each be configured as a graphical marking on a surface of the ancillary element, in particular on different surfaces or the same surface of the ancillary element, and/or as a structural element of the ancillary element.

The ancillary element may advantageously be configured to be arranged in the defined arrangement in respect of the orientation element, in particular in a relative positioning in respect of the orientation element. In particular, the ancillary element may be arranged on the orientation element, in particular stationary, in the defined arrangement and/or integrated in the defined arrangement into the orientation element. Alternatively, the ancillary element may be repositionable, in particular translatable and/or rotatable, in respect of the orientation element. For example, the ancillary element may be configured to be repositioned into the defined arrangement in respect of the orientation element. Further, the ancillary element may be configured to be attached in the defined arrangement to the orientation element and/or, for the defined arrangement, to be introduced at least partially into the orientation element.

The identification marker, in particular the first subsidiary identification marker, may advantageously be arranged on the ancillary element, such that the identification marker, in particular the first subsidiary identification marker, is arranged in the center of rotation if the ancillary element is arranged in the defined arrangement in respect of the orientation element.

The light guiding device may advantageously include a light source, (e.g., a laser light source), which is configured to emit the predefined distribution of light. For this, the light guiding device may include an optical aperture. The predefined distribution of light may advantageously be a normal distribution of light from a normal light source for the visualization of a path, in particular a needle path. In particular, the predefined distribution of light may include a predefined distribution of laser light. In this case, the predefined distribution of light may project a predefined light pattern, for example intersecting lines and/or a point. Thanks to the predefined distribution of light the specified path, in respect of which the medical object is to be oriented in the defined positional relationship, may be projected. The predefined light pattern may be generated, in particular provided, by reflection and/or absorption of at least part of the predefined distribution of light by the identification marker.

The predefined distribution of light, in particular a point of intersection of the projected intersecting lines and/or the projected point, may advantageously, when the center of rotation is arranged on the path, illuminate the identification marker, in particular the first subsidiary identification marker. In particular, the predefined distribution of light, in particular a point of intersection of the projected intersecting lines and/or the projected point, may illuminate the identification marker, in particular the first subsidiary identification marker, if and only if the center of rotation is arranged on the path. For the arrangement of the center of rotation on the path the guide element may be configured to be repositionable, for example translatable and/or rotatable. The defined arrangement of orientation element and ancillary element may advantageously remain unaffected when the guide element is repositioned.

The arrangement, in particular the defined arrangement or a further arrangement, of orientation element and ancillary element may be movable, in particular rotatable, about the center of rotation arranged on the path in an operating state of the device, such that the predefined distribution of light illuminates the identification marker with the predefined light pattern, in particular if and only if the guide axis of the orientation element is oriented in the defined positional relationship in respect of the path. The defined positional relationship may describe a relative positioning between the guide axis of the orientation element and the specified path. In particular, the defined positional relationship may specify a parallel orientation of the guide axis of the orientation element in respect of the specified path and/or an orientation of the guide axis of the orientation element along the specified path. Alternatively, the defined positional relationship may specify an orientation of the guide axis of the orientation element at a defined angle, in particular an angle of intersection between guide axis and specified path or an angle at a specified spatial distance between guide axis and specified path, in respect of the specified path.

The proposed form of embodiment may advantageously enable a time-efficient, precise, and intuitive orientation of the medical object in the defined positional relationship in respect of the specified path.

In a further advantageous form of embodiment of the proposed device, the orientation element may have a tubular sleeve which is configured to receive the medical object and to guide it along the guide axis.

The tubular sleeve may be configured to be substantially cylindrical. In particular, the tubular sleeve may have a casing made from a substrate, in particular with a round or angular cross-section, which surrounds a hollow space. The tubular sleeve may further have two openings along its direction of longitudinal extent, in particular on one of two end faces in each case. In this case, the medical object may be introduced through the first opening in the sleeve into the hollow space of the sleeve, in particular of the casing, and may be brought out through the second opening in the sleeve. Further, the sleeve may be configured to guide the medical object along the guide axis, in particular by mechanical interaction with the casing of the sleeve. When the sleeve is configured to be substantially cylindrical, the guide axis may run parallel to a longitudinal axis, in particular an axis of symmetry, of the cylinder.

The proposed form of embodiment may advantageously enable the medical object to be guided safely and precisely along the guide axis.

In a further advantageous form of embodiment of the proposed device, the ancillary element may have at least one disk-shaped section. In this case, the identification marker may be arranged on a flat side of the at least one disk-shaped section and/or may be integrated into the at least one disk-shaped section.

The disk-shaped section may be formed from a substrate and/or as substantially flat. In this case, the disk-shaped section may have at least one flat side. The at least one flat side may advantageously in the defined arrangement of the ancillary element face the light guiding device, in particular the light source. Further, the disk-shaped section, in particular the flat side of the disk-shaped section, may in the defined arrangement be arranged at an angle, in particular at a right angle, in respect of a direction of light incidence of the distribution of light emitted by the light guiding device, if the guide axis of the orientation element is oriented in the defined positional relationship in respect of the path. The identification marker, in particular the first and/or the second subsidiary identification marker, may advantageously be arranged on the at least one flat side of the at least one disk-shaped section, for example as a graphical marking, and/or may be integrated into the at least one disk-shaped section, for example as a structural element. As a result, the predefined distribution of light may illuminate the at least one flat side of the disk-shaped section when the center of rotation is arranged on the path.

In a further advantageous form of embodiment of the proposed device, the orientation element may be movably mounted so as to be forcibly guided by the guide element about at least one axis of rotation which runs through the center of rotation.

The guide element may advantageously be configured to restrict the degrees of freedom of movement of the orientation element to a rotation about the at least one axis of rotation, in particular multiple axes of rotation, the at least one axis of rotation running through the center of rotation. In particular, the guide element may be configured to block a translational motion of the orientation element in respect of the center of rotation by the forced guidance. The at least one axis of rotation may describe a spatial axis that runs through the center of rotation and about which the orientation element is movably, in particular rotatably, mounted.

If the guide element is configured to restrict the degrees of freedom of movement of the orientation element to a rotation about precisely one axis of rotation, the axis of rotation running through the center of rotation, the orientation element may be movably, in particular rotatably, mounted within a plane which runs perpendicular to the axis of rotation and through the center of rotation.

In a further advantageous form of embodiment of the proposed device, the orientation element may be movably mounted so as to be forcibly guided by the guide element about two different axes of rotation which run through the center of rotation.

The two different axes of rotation may advantageously intersect in the center of rotation. In this case, the two different axes of rotation may have a specified angle, for example a right angle, to one another in the center of rotation. The guide element may be configured to restrict the degrees of freedom of movement of the orientation element to a rotation about the two different axes of rotation. The orientation element may be mounted so as to be movable, in particular rotatable, in a forcibly guided manner by the guide element on a spherical shell about the center of rotation, in particular about the two different axes of rotation.

The guide element may be configured as an, in particular motorized, cardanic suspension, (e.g., a gimbal). The proposed form of embodiment may enable a particularly flexible, in particular three-dimensional, repositioning of the defined arrangement of orientation element and ancillary element about the center of rotation.

In a further advantageous form of embodiment of the proposed device, the light guiding device may be configured to emit the predefined distribution of light containing multiple light arrays or light fans or light fan beams, which do not run parallel to one another and intersect along the path.

The light guiding device may be configured to generate the multiple light arrays in multiple planes by emitting the predefined distribution of light, wherein the multiple planes intersect along the path and do not run parallel to one another. A line of intersection of the multiple planes, in particular of the multiple light arrays, may form the specified path. In this case, one of the multiple light arrays may in each case be formed by multiple light beams which in each case run within one of the multiple planes, for example in a fan shape and/or parallel to one another. By emitting the predefined distribution of light, containing the multiple light arrays, intersecting lines may be projected by the light guiding device. In this case, a point of intersection of the intersecting lines may lie on the path, in particular may mark the path. For this, the light guiding device may include two crossed line lasers.

In particular, the light guiding device may be configured to emit the predefined distribution of light, containing two light arrays, the light arrays running at right angles to one another and intersecting along the path. As a result, a precise and readily determinable specification of the path may be enabled by the predefined distribution of light. In particular, when the guide axis of the orientation element is arranged in the defined positional relationship in respect of the path, the predefined distribution of light may project the predefined light pattern by the multiple light arrays onto the identification marker.

In a further advantageous form of embodiment of the proposed device, the device may further include at least one selectively activatable locking element. The locking element may be configured, on activation, to block the repositioning of the center of rotation. Alternatively or additionally, the at least one locking element may be configured, on activation, to restrict the movability of the orientation element to a rotation about an axis of rotation which runs through the center of rotation.

The at least one locking element may be configured to be activated manually, semi-automatically, and/or fully automatically, in particular if the center of rotation is arranged on the specified path. For a manual and/or semi-automatic activation, the at least one locking element may include an input device, (e.g., a key and/or a button and/or a switch and/or a pedal and/or a lever), and/or an, in particular mechanical, locking mechanism or device, (e.g., a locking screw and/or a screw nut and/or a clamping lever), which may be activated, in particular manipulated, by a medical operative. Alternatively or additionally, the device may be configured to detect, in particular automatically, whether the center of rotation is arranged on the path, and if so to activate the at least one locking element, for example, electromagnetically and/or in a motorized manner and/or robotically. For this, the device, in particular the ancillary element, may include a sensor, for example an optical and/or electromagnetic sensor, (e.g., a photosensor), which is configured to detect whether the identification marker is illuminated with the predefined distribution of light. For this, the sensor may be integrated into the identification marker and/or may be arranged on the identification marker.

If the guide element has multiple axes of movement, (e.g., joints and/or hinges), the at least one locking element may advantageously be configured to block at least one of the axes of movement, in particular several of the axes of movement, on activation. Furthermore, the at least one locking element may be configured to be deactivated manually, semi-automatically, and/or fully automatically, in particular if the center of rotation is not arranged on the path. In this case, the at least one locking element may be configured, on deactivation, to unblock the repositioning of the center of rotation, in particular of the guide element.

The at least one locking element may advantageously be configured, on activation, to block only the repositioning of the center of rotation, in particular of the guide element, wherein further a rotation of the orientation element about the center of rotation is possible, in particular without restriction.

Alternatively or additionally, the at least one locking element may be configured, on activation, to restrict the movability of the orientation element to a rotation about an axis of rotation which runs through the center of rotation. The device may advantageously be configured to detect whether the center of rotation is arranged on the path, for example by the sensor, and if so to restrict the movability of the orientation element to a rotation about an axis of rotation which runs through the center of rotation, in particular perpendicular to the path. In this case, the at least one locking element may be configured, on deactivation, to unblock the movability of the orientation element.

The proposed form of embodiment may advantageously provide the movability of the arrangement of orientation element and ancillary element about a center of rotation.

In a further advantageous form of embodiment of the proposed device, the ancillary element may be attached in the defined arrangement to the orientation element and/or may be integrated into the orientation element.

The ancillary element may advantageously in the defined arrangement be attached, in particularly detachably, to the orientation element. For example, the ancillary element may in the defined arrangement be coupled mechanically and/or electromagnetically to the orientation element.

Alternatively or additionally, the ancillary element may be integrated into the orientation element. For example, the orientation element may have the identification marker, which may be illuminated by the predefined distribution of light and arranged in the defined arrangement in respect of the orientation element. The identification marker, in particular in a disk-shaped embodiment, may advantageously be arranged in the defined arrangement at an angle in respect of the guide axis.

By the proposed form of embodiment, it may advantageously be provided that the defined arrangement is retained even if the orientation element moves about the center of rotation.

In a further advantageous form of embodiment of the proposed device, the ancillary element may be repositionable in a longitudinally guided manner in the defined positional relationship in respect of the guide axis from the defined arrangement to a further arrangement. In this case, the further arrangement of orientation element and ancillary element may be movable about the center of rotation, such that the predefined distribution of light illuminates the identification marker with the predefined light pattern, in particular if and only if the guide axis of the orientation element is oriented in the defined positional relationship in respect of the path.

The ancillary element may advantageously be mounted by an, in particular mechanical and/or electromagnetic, coupling, in particular to the guide element and/or the orientation element, in the defined positional relationship in respect of the guide axis so as to be movable, in particular translatable, in a longitudinally guided manner. For this, the ancillary element may have a first coupling element, (e.g., a recess, in particular a groove and/or a sleeve), and/or an elevation, (e.g., a spring and/or a rod and/or pin). Further, the guide element and/or the orientation element may have a second coupling element, for example, a recess and/or an elevation. The first and the second coupling element may be configured, for the mechanical coupling of the ancillary element to the guide element and/or the orientation element, to be brought into mechanical engagement. Further, the first and the second coupling element may be configured to restrict a movability, (e.g., degrees of freedom of movement), of the ancillary element to a movement, (e.g., a translational motion), of the ancillary element in the defined positional relationship in respect of the guide axis from the defined arrangement to the further arrangement.

The further arrangement of the ancillary element in respect of the orientation element may be different from the defined arrangement of the ancillary element in respect of the orientation element. In particular, it is possible to reposition the ancillary element manually, semi-automatically, and/or fully automatically from the defined arrangement to the further arrangement. For example, the ancillary element may be configured to be repositioned by manual engagement by a medical operative from the defined arrangement to the further arrangement. Alternatively or additionally, the ancillary element may be configured to be repositioned in a motorized and/or robotic manner, in particular semi-automatically and/or fully automatically, from the defined arrangement to the further arrangement.

By repositioning the ancillary element from the defined arrangement, longitudinally guided in the defined positional relationship in respect of the guide axis, to the further arrangement an improved, in particular more intuitive, rotation of the arrangement of orientation element and ancillary element about the center of rotation may be enabled.

In a further advantageous form of embodiment of the proposed device, the ancillary element may be configured to be introduced at least partially into the sleeve. In this case, the ancillary element may in the defined arrangement be introduced at least partially into the sleeve.

The ancillary element may be configured to be introduced, at least partially, in particular completely, into the sleeve, in particular into a hollow space inside the casing of the sleeve, in particular via the first opening in the sleeve. For this, the ancillary element may have a first, in particular rod-shaped, section, wherein an external diameter of the first section is smaller than an internal diameter of the casing of the sleeve. The first, in particular rod-shaped, section may be configured to be substantially elongated. In this case, a longitudinal axis of the first section in the defined arrangement may be arranged parallel to the guide axis of the orientation element. The identification marker may define a plane, into which the light guiding device projects the defined light pattern in the operating state of the device, in which the guide axis of the orientation element is arranged in the defined positional relationship in respect of the path. In this case, the plane may be arranged at a specified angle, in particular a right angle, in respect of the longitudinal axis of the first, in particular rod-shaped, section of the ancillary element. If the ancillary element has a disk-shaped section with the identification marker, the plane may be arranged in parallel to the disk-shaped section. As a result, it may advantageously be provided that the identification marker with the predefined light pattern is illuminated if and only if the guide axis is arranged in the predefined positional relationship in respect of the path.

In a further advantageous form of embodiment of the proposed device, the ancillary element and/or the orientation element may have a positioning mechanism or device which blocks an introduction of the ancillary element into the sleeve any further than the defined arrangement.

The ancillary element and the orientation element may each have a positioning mechanism or device that blocks the introduction of the ancillary element into the sleeve, in particular mechanically and/or electromagnetically, any further than the defined arrangement. Alternatively, the ancillary element or the orientation element may have a positioning mechanism or device that blocks the introduction of the ancillary element into the sleeve, in particular mechanically and/or electromagnetically, any further than the defined arrangement. The positioning device may be configured as a structural feature of the orientation element and/or of the ancillary element, for example, as a recess and/or elevation. In particular, the positioning device may be configured, on achievement of the defined arrangement, to create a mechanical engagement between the ancillary element and the orientation element which mechanically blocks the further introduction of the ancillary element into the sleeve. For example, the positioning device may provide an anchor point and/or trigger point between the ancillary element and the orientation element, which mechanically blocks the further introduction of the ancillary element into the sleeve by attachment and/or triggering of the ancillary element. Alternatively or additionally, the positioning device may be configured, when the ancillary element is introduced into the sleeve any further than the defined arrangement, to exert an electromagnetic force on the ancillary element, which is opposite to a direction for the introduction of the ancillary element into the sleeve and which electromagnetically blocks the further introduction of the ancillary element into the sleeve.

As a result, a particularly intuitive arrangement of the ancillary element in the defined arrangement in respect of the orientation element may be enabled.

In a further advantageous form of embodiment of the proposed device, the ancillary element may have a rod-shaped section which is configured to be introduced at least partially into the sleeve. Further, the ancillary element may have a further section that forms the positioning the ancillary element and mechanically blocks the introduction of the ancillary element into the sleeve any further than the defined arrangement.

The rod-shaped section may be configured as substantially cylindrical and elongated. Further, the rod-shaped section may have an external diameter which is smaller than an internal diameter of the casing of the sleeve. The rod-shaped section may advantageously be configured to be introduced, at least partially, in particular completely, into the sleeve, in particular along the guide axis and/or parallel to the guide axis. Further, the ancillary element may have a further section that forms the positioning the ancillary element. The further section may have an elevation and/or an, in particular disk-shaped, form, wherein an external diameter of the further section is larger than the internal diameter of the casing of the sleeve. As a result, the further section may mechanically block the introduction of the ancillary element, in particular of the rod-shaped section, into the sleeve, in particular into the hollow space of the sleeve, any further than the defined arrangement. The further section may have an anchor point and/or an anchor surface that, in the defined arrangement of the ancillary element in respect of the orientation element, mechanically contacts or touches the sleeve, (e.g., the casing of the sleeve).

As a result, a particularly intuitive arrangement of the ancillary element in the defined arrangement in respect of the orientation element may be enabled.

In a further advantageous form of embodiment of the proposed device, the ancillary element and/or the orientation element may have a display mechanism or device which displays the defined arrangement of the ancillary element in respect of the orientation element.

The ancillary element and the orientation element may each have a display mechanism or device. Alternatively, the ancillary element or the orientation element may have a display mechanism or device. The display device may be configured to display the defined arrangement of the ancillary element in respect of the orientation element by outputting an acoustic and/or visual and/or haptic signal. The display device may include a graphical marking, (e.g., a line and/or a point and/or a pattern and/or a cross), and/or a structural element, (e.g., a recess and/or an elevation and/or an edge), and/or lighting mechanism or device, (e.g., a light-emitting diode (LED)), which is configured to display the defined arrangement of the ancillary element in respect of the orientation element. For example, the graphical marking and/or the structural element of the ancillary element may in the defined arrangement of the ancillary element in respect of the orientation element be arranged flush with and/or in alignment with a further graphical marking and/or a further structural element of the orientation element. Alternatively or additionally, the lighting device may display the defined arrangement by emitting a light signal. For this, the ancillary element and/or the orientation element may have a positioning sensor configured to detect whether the ancillary element is arranged in the defined arrangement in respect of the orientation element. If so, the positioning sensor may provide a signal to the display element, whereupon the display element displays the defined arrangement of the ancillary element in respect of the orientation element.

Further, the display device may be configured as a brake, (e.g., a mechanical and/or electromagnetic brake) and/or as an engagement point, (e.g., a mechanical and/or electromagnetic engagement point), between the ancillary element and the orientation element. The brake may, on achievement of the defined arrangement, exert a force on the ancillary element which is opposite to a direction of movement of the ancillary element, in particular the direction for the introduction of the ancillary element into the sleeve. Further, the engagement point may be configured, when the ancillary element leaves the defined arrangement, in particular when the ancillary element moves away out of the defined arrangement, to exert a force on the ancillary element that is opposite to a direction of movement for leaving the defined arrangement. In this case, the display device may be configured to display the defined arrangement of the ancillary element in respect of the orientation element as a haptic signal, in particular haptic feedback.

As a result, a particularly intuitive arrangement of the ancillary element in the defined arrangement in respect of the orientation element may be enabled.

A second aspect of the disclosure relates to a system that includes a proposed device for orienting a medical object in respect of an object under examination and a navigation unit. In this case, the navigation unit includes a medical imaging device and/or a medical navigation system and/or a medical treatment system. Further, the light guiding device is arranged on the navigation unit and/or is integrated into the navigation unit.

The advantages of the proposed system substantially correspond to the advantages of the proposed device for orienting a medical object in respect of an object under examination. Features, advantages, or alternative forms of embodiment mentioned here may likewise also be transferred to the other claimed subject matters and vice versa.

The medical imaging device may include a medical X-ray device and/or a magnetic resonance tomography installation (MRT installation) and/or a computed tomography installation (CT installation) and/or a positron emission tomography installation (PET installation) and/or an ultrasound device. In this case, the medical imaging device may be configured to acquire medical image data of the object under examination. The light guiding device may be arranged on the medical imaging device and/or may be integrated into the medical imaging device.

The medical navigation system may be integrated into the medical imaging system and/or into the medical treatment system. Alternatively, the medical navigation system may be realized separately, in particular autonomously. The medical navigation system may have a sensor, (e.g., a visual and/or electromagnetic and/or acoustic, in particular ultrasound-based, sensor), which is configured to detect, in particular to locate and/or track, the object under examination. In particular, the medical navigation system may be configured to detect an, in particular current, positioning, in particular a position and/or orientation and/or pose, of the object under examination. The medical navigation system may further be configured to provide the navigation data containing information on the, in particular current, positioning of the object under examination. The light guiding device may be arranged on the medical navigation system and/or may be integrated into the medical navigation system.

The medical treatment system may include a medical X-ray installation and/or a therapeutic ultrasound device. In this case, the light guiding device may be arranged on the medical treatment system and/or may be integrated into the medical treatment system.

The system, in particular the navigation unit, may be configured to control the emission of the specified distribution of light by the light guidance unit, such that the specified path is adjustable, for example as a function of medical image data acquired by the medical imaging device and/or of navigation data captured by the medical navigation system and/or of a treatment plan of the medical treatment system. For this, the light guiding device may be arranged, so as to be movably mounted, in particular rotatably and/or translatably and/or pivotably, on the navigation unit and/or may be integrated into the navigation unit. Alternatively or additionally, the light guiding device may be configured to adjust the specified distribution of light as a function of medical image data acquired by the medical imaging device and/or of navigation data captured by the medical navigation system and/or of a treatment plan of the medical treatment system. In particular, the navigation unit may be configured to register medical image data, in particular preoperative and/or intraoperative medical image data, and/or a planning dataset of the object under examination with the navigation data of the medical navigation system and to adjust the specified path to the current positioning of the object under examination. In this case, the planning dataset may contain path planning for positioning the medical object in respect of the object under examination.

A third aspect of the disclosure relates to a method for orienting a medical object by a proposed device for orienting a medical object in respect of an object under examination. In this case, the predefined distribution of light is emitted by the light guiding device. Further, the guide element is repositioned, such that the predefined distribution of light illuminates the identification marker of the ancillary element. In this case, the center of rotation is arranged on the path specified by the predefined distribution of light and at a distance from the object under examination. Further, the arrangement, forcibly guided by the guide element, of orientation element and ancillary element about the center of rotation is repositioned, such that the predefined distribution of light illuminates the identification marker with the predefined light pattern. In this case, the guide axis of the orientation element is oriented in the predefined positional relationship to the path. Further, the medical object is arranged and/or moved along the guide axis by the orientation element.

The advantages of the proposed method substantially correspond to the advantages of the proposed device for orienting a medical object in respect of an object under examination and/or of the proposed system. Features, advantages, or alternative forms of embodiment mentioned here may likewise be transferred to the other claimed subject matters and vice versa.

In a further advantageous form of embodiment of the proposed method, the ancillary element may be arranged prior to the repositioning of the guide element in the defined arrangement in respect of the orientation element. Further, the ancillary element can, following the arrangement of the center of rotation on the path and prior to the repositioning of the forcibly guided arrangement, be repositioned in a longitudinally guided manner in the defined positional relationship in respect of the guide axis from the defined arrangement to a further arrangement.

BRIEF DESCRIPTION OF THE DRAWINGS

Exemplary embodiments of the disclosure are represented in the drawings and are described in greater detail below. The same reference characters are used for the same features in different figures. In the drawings.

DETAILED DESCRIPTION

Figure 1:
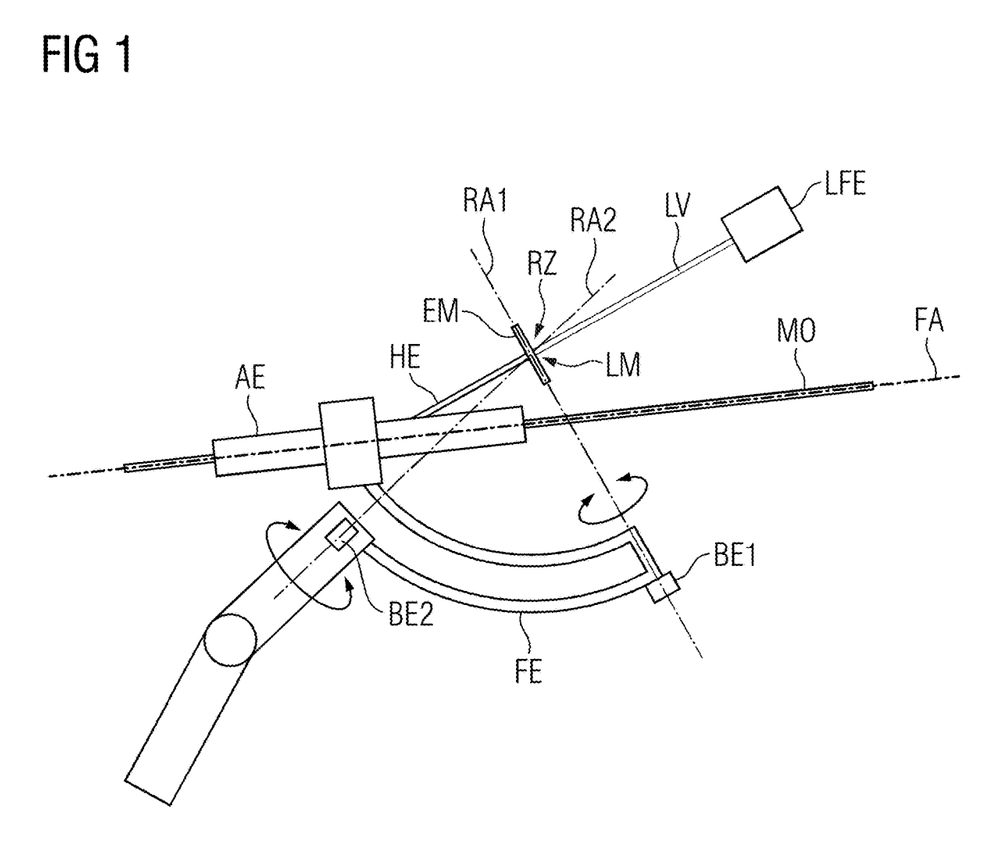
FIG. 1 depicts a schematic representation of an advantageous form of embodiment of a proposed device for orienting a medical object in respect of an object under examination.

FIG. 1 schematically shows an advantageous form of embodiment of a proposed device for orienting a medical object MO in respect of an object under examination. In this case, the device may include an orientation element AE, a guide element FE, an ancillary element HE, and a light guiding device LFE. The orientation element AE may be mounted by the guide element FE about a center of rotation RZ in a forcibly guided manner. In particular, the orientation element AE may be movably mounted so as to be forcibly guided by the guide element FE about two different axes of rotation RA1 and RA2, which run through the center of rotation RZ. The ancillary element HE may have an identification marker EM. Furthermore, the ancillary element HE may be arrangeable in a defined arrangement in respect of the orientation element AE, such that the identification marker EM is arranged in the center of rotation RZ. Further, the light guiding device LFE may be configured to emit a predefined distribution of light LV that specifies a path. In this case, the predefined distribution of light LV may illuminate the identification marker EM when the center of rotation RZ is arranged on the path at a distance from the object under examination. The arrangement of orientation element AE and ancillary element HE may be movable about the center of rotation RZ arranged on the path in an operating state of the device, such that the predefined distribution of light LV illuminates the identification marker EM with a predefined light pattern LM, if the guide axis FA of the orientation element AE is oriented in a defined positional relationship in respect of the path.

The orientation element AE may advantageously have a tubular sleeve configured to receive the medical object MO and to guide the medical object MO along the guide axis FA. Further, the ancillary element HE may have at least one disk-shaped section. In this case, the identification marker EM may be arranged on a flat side of the at least one disk-shaped section and/or may be integrated into the at least one disk-shaped section.

The light guiding device LFE may advantageously be configured to emit the predefined distribution of light LV containing multiple fans or multiple light fan beams that do not run parallel to one another and intersect along the path.

The device may further include two selectively activatable locking elements BE1 and BE2 which are configured, on activation, to block the repositioning of the center of rotation RZ and/or to restrict a movability of the orientation element AE to a rotation about one of the axes of rotation RA1 or RA2 which run through the center of rotation RZ.

In the defined arrangement, the ancillary element HE may be attached to the orientation element AE and/or may be integrated into the orientation element AE.

FIGS. 2 to 5 show schematic representations of different operating states of a further advantageous form of embodiment of a proposed device for orienting a medical object MO in respect of an object under examination. In this case, the ancillary element HE may be configured to be introduced at least partially into the sleeve. Further, the ancillary element HE may have a positioning mechanism or device PE that blocks an introduction of the ancillary element HE into the sleeve any further than the defined arrangement. The ancillary element HE may advantageously have a rod-shaped section configured to be introduced at least partially into the sleeve. Further, the ancillary element may have a further section that forms the positioning mechanism or device PE of the ancillary element HE and mechanically blocks the introduction of the ancillary element HE into the sleeve any further than the defined arrangement. Further, the orientation element AE may have a display mechanism or device AZ that displays the defined arrangement of the ancillary element HE in respect of the orientation element AE.

Figure 2:
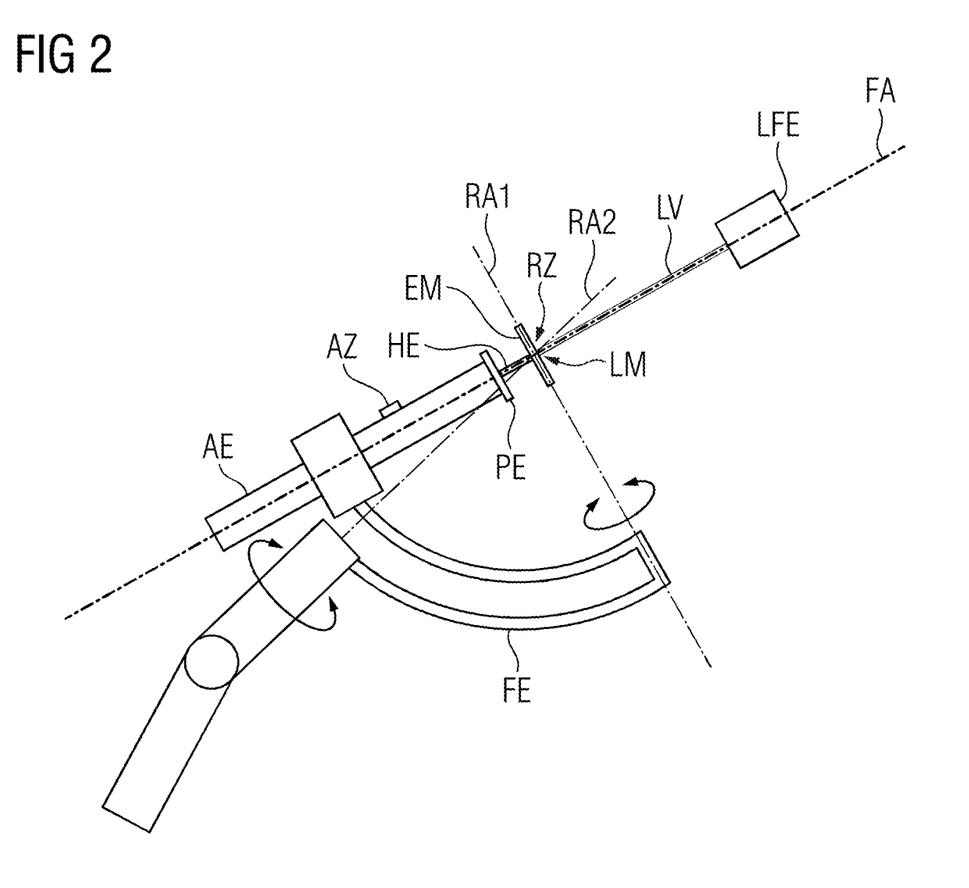
FIGS. 2 to 5 depict schematic representations of different operating states of a further advantageous form of embodiment of a proposed device for orienting a medical object in respect of an object under examination.
Figure 3:
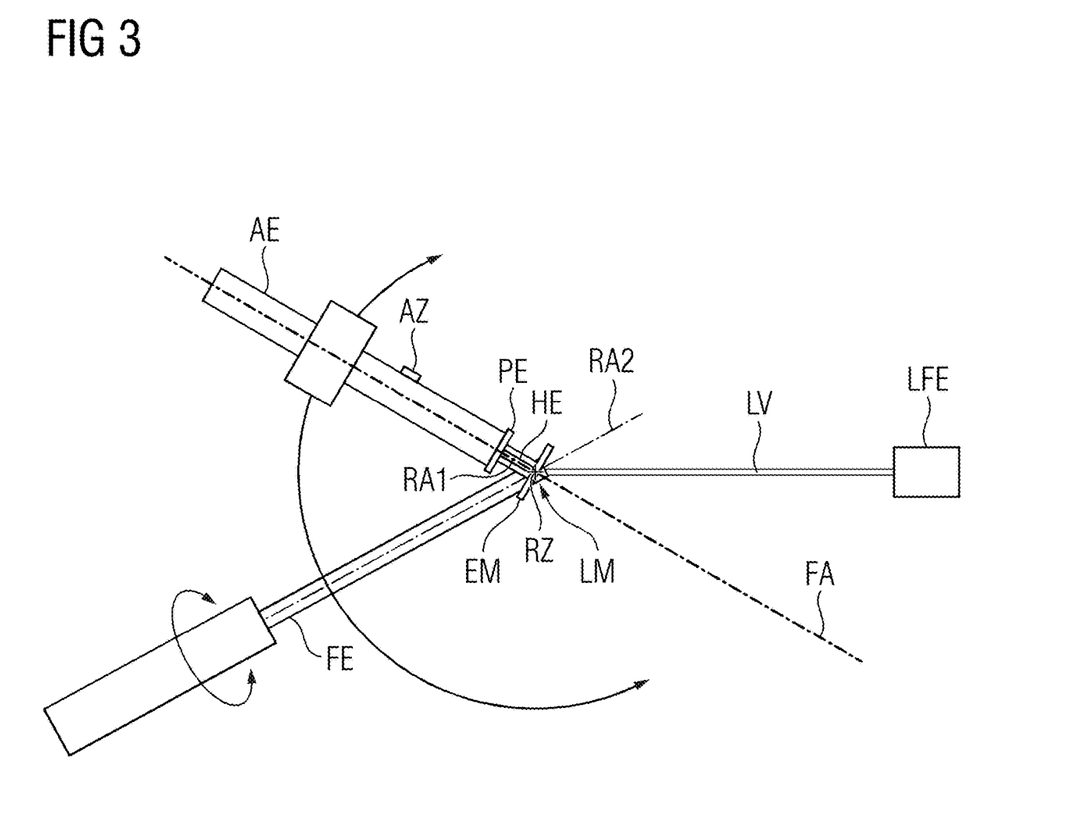

FIGS. 2 and 3 show schematic representations of an operating state of the device from different viewing angles, in which the ancillary element HE is arranged in the defined arrangement in respect of the orientation element AE. In this case, the ancillary element HE in the defined arrangement may be introduced at least partially into the sleeve. Further, in the operating state the guide element FE may be positioned, such that the center of rotation RZ is arranged on the path. In this case, the predefined distribution of light LV may illuminate the identification marker EM.

Figure 4:
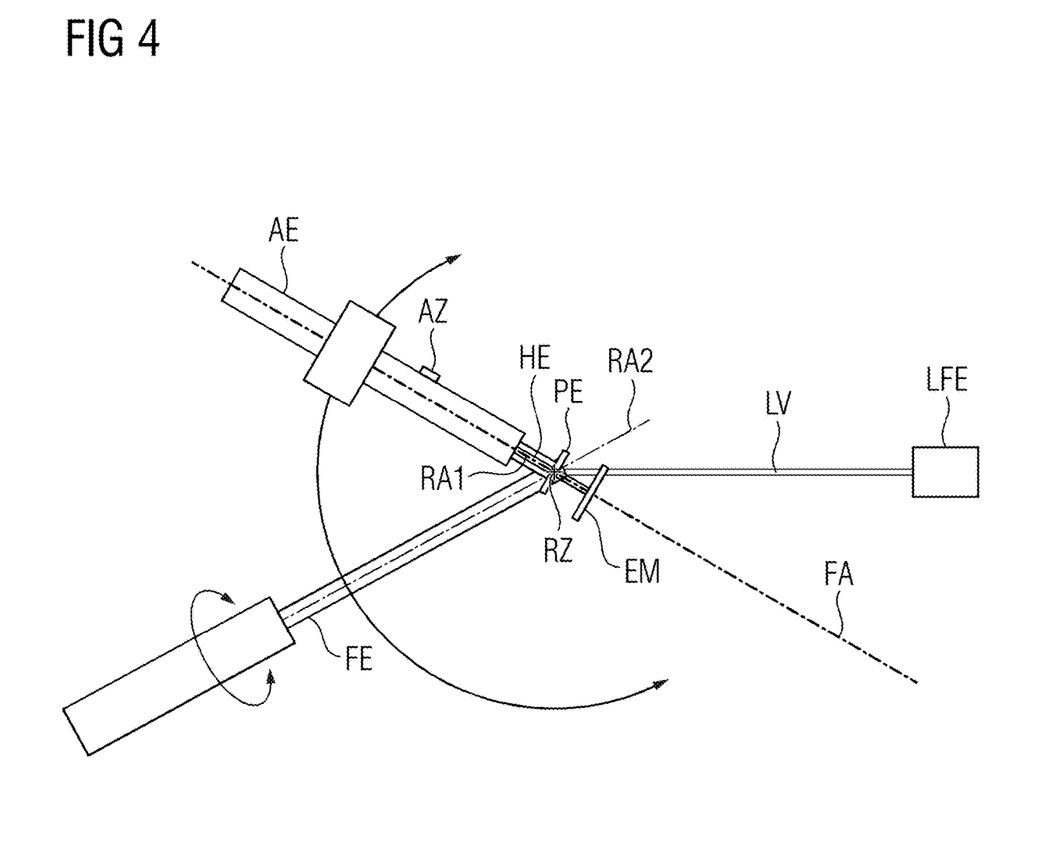
Figure 5:
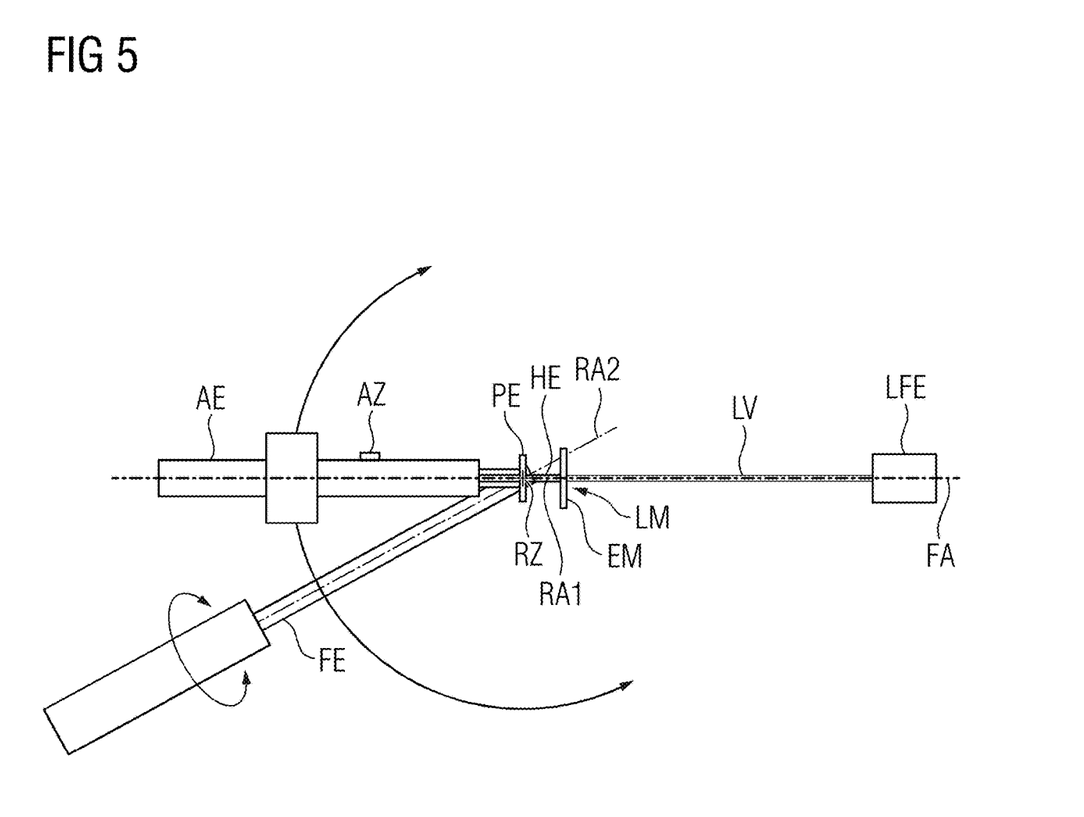

The ancillary element HE may be repositionable in a longitudinally guided manner in the defined positional relationship in respect of the guide axis FA from the defined arrangement to a further arrangement. FIG. 4 schematically represents a further operating state of the device, in which the ancillary element HE is arranged in the further arrangement in respect of the orientation element AE. FIG. 5 shows a schematic representation of a further operating state of the device, in which the further arrangement of orientation element AE and ancillary element HE has been repositioned about the center of rotation RZ, such that the predefined distribution of light LV illuminates the identification marker EM with the predefined light pattern LM. In this case, the guide axis FA of the orientation element AE may be oriented in the defined positional relationship in respect of the path. Further, in this case the identification marker EM may be arranged at a further point on the path specified by the distribution of light LV, the further point being different from the center of rotation RZ.

The guide axis FA, the center of rotation RZ, the defined arrangement, and/or the further arrangement may advantageously be defined in a coordinate system of the orientation element AE that moves along with the movement of the orientation element AE. Furthermore, the path specified by the distribution of light LV may be defined in a coordinate system, (e.g., non-moving coordinate system), of the surrounding space, (e.g., relative to the object under examination), of a patient positioning device, a navigation unit, and/or the light guiding device LFE.

Figure 6:
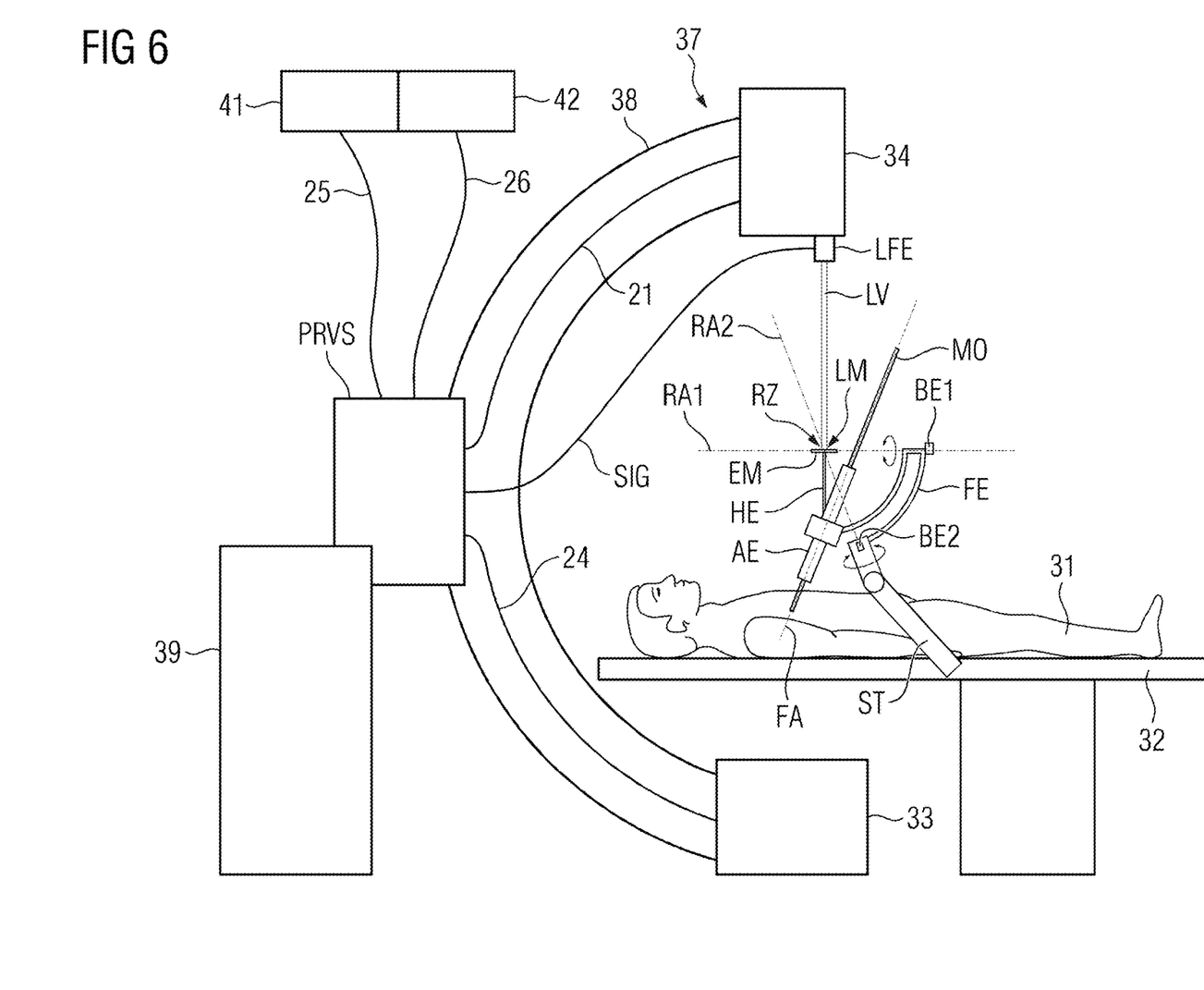
FIG. 6 depicts a schematic representation of an advantageous form of embodiment of a proposed system.

FIG. 6 shows a schematic representation of an advantageous form of embodiment of a proposed system. In this case, the system may include a proposed device for orienting a medical object MO and a navigation unit. In this case, the navigation unit may include a medical imaging system and/or a medical navigation system and/or a medical treatment system. In FIG. 6, the navigation unit includes, by way of example of a medical imaging system, a medical C-arm X-ray device 37. The light guiding device LFE may advantageously be arranged on the navigation unit, in particular the medical C-arm X-ray device 37, and/or may be integrated into the navigation unit, in particular the medical C-arm X-ray device 37. As represented in FIG. 6, the light guiding device LFE may be arranged on a detector 34 of the medical C-arm X-ray device 37.

In this case, the medical C-arm X-ray device 37 may be configured to acquire medical image data of an object under examination 31, arranged on a patient positioning device 32, and to provide the medical image data to a provision unit PRVS. The guide element FE may be arranged on, in particular attached to, the patient positioning device 32 and/or the navigation unit, in particular the medical C-arm X-ray device 37, by a mechanical arm and/or stand and/or robot arm ST. The medical C-arm X-ray device 37 may advantageously contain the detector 34, in particular an X-ray detector, and a source 33, in particular an X-ray source. To acquire the medical image data, a C-arm 38 of the C-arm X-ray device 37 may be movably mounted about one or more axes. Further, the medical C-arm X-ray device 37 may include a movement unit 39 configured to move the medical C-arm X-ray device 37 in space. To acquire the medical image data of the object under examination 31, the provision unit PRVS may send a signal 24 to the X-ray source 33. The X-ray source 33 may then emit an X-ray beam. When the X-ray beam, following an interaction with the object under examination 31, strikes a surface of the detector 34, the detector 34 may send a signal 21 to the provision unit PRVS. On the basis of the signal 21, the provision unit PRVS may receive the medical image data. The provision unit PRVS may further be configured to control the light guiding device LFE, (e.g., by a signal SIG). In particular, the provision unit PRVS may be configured to control the light guiding device LFE as a function of the medical image data, in particular by the signal SIG, in order to emit the specified distribution of light LV.

The system may further have an input unit 42, (e.g., a keyboard), and a display unit 41, (e.g., a monitor and/or a display and/or a projector). The input unit 42 may be integrated into the display unit 41, for example, in the case of a capacitive and/or resistive input display. The input unit 42 may advantageously be configured to capture a user input. For this, the input unit 42 may send a signal 26 to the provision unit PRVS. The provision unit PRVS may be configured to control the medical C-arm X-ray device 37 and/or the light guiding device LFE as a function of the user input, in particular as a function of the signal 26. The display unit 41 may advantageously be configured to display a graphical representation of the medical image data. For this, the provision unit PRVS may send a signal 25 to the display unit 41.

Figure 7:
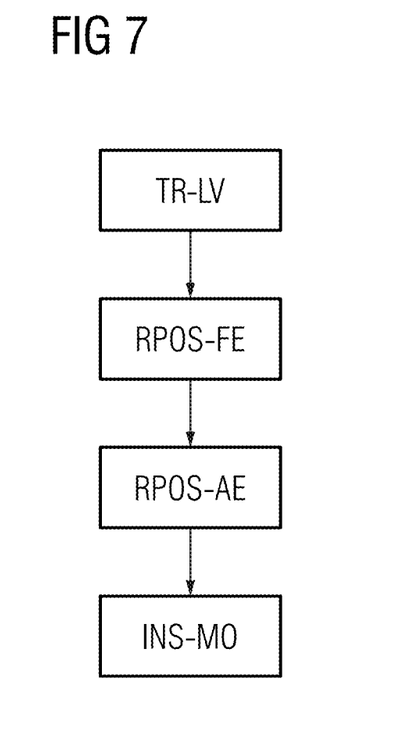
FIG. 7 depicts a schematic representation of an advantageous form of embodiment of a proposed method for orienting a medical object.

FIG. 7 schematically represents an advantageous form of embodiment of a proposed method for orienting a medical object MO. In this case, the predefined distribution of light LV may be emitted TR-LV by the light guiding device LFE. Further, the guide element FE may be repositioned RPOS-FE, such that the predefined distribution of light LV illuminates the identification marker EM of the ancillary element HE. In this case, the center of rotation RZ may be arranged on the path specified by the predefined distribution of light LV and at a distance from the object under examination 31. Further, the arrangement of orientation element AE and ancillary element HE forcibly guided by the guide element FE may be repositioned RPOS-AE about the center of rotation RZ, such that the predefined distribution of light LV illuminates the identification marker EM with the predefined light pattern LM. The guide axis FA of the orientation element AE may be oriented in the defined positional relationship to the path. Furthermore, the medical object MO may be arranged and/or moved INS-MO along the guide axis FA by the orientation element AE.

The ancillary element HE may advantageously be arranged prior to the repositioning RPOS-FE of the guide element FE in the defined arrangement in respect of the orientation element AE. In this case, the ancillary element HE may, following the arrangement of the center of rotation RZ on the path and prior to the repositioning RPOS-AE of the forcibly guided arrangement, be repositioned in a longitudinally guided manner in the defined positional relationship in respect of the guide axis FA from the defined arrangement to the further arrangement.

The schematic representations contained in the described figures are in no way to scale or in proportion.

In conclusion, it is once again noted that the methods and devices described in detail above relate solely to exemplary embodiments that may be modified by the person skilled in the art in a variety of ways, without departing from the scope of the invention. Further, the use of the indefinite article "a" or "an" does not rule out that the features in question may also be present multiple times. Likewise, the terms "unit" and "element" do not rule out that the components in question include multiple interacting subcomponents, which, if appropriate, may also be distributed spatially.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A device for orienting a medical object in respect of an object under examination, the device comprising:
   an orientation element;
   a guide element;
   an ancillary element; and
   a light guiding device,
   wherein the orientation element is movably mounted so as to be forcibly guided by the guide element about a center of rotation, the center of rotation being repositionable by repositioning the guide element,
   wherein the orientation element is configured for a longitudinal guidance of the medical object along a guide axis specified by the orientation element,
   wherein the ancillary element has an identification marker,
   wherein the ancillary element is configured to be arranged in a defined arrangement in respect of the orientation element, such that the identification marker is arranged in the center of rotation,
   wherein the light guiding device is configured to emit a predefined distribution of light that specifies a path,
   wherein the predefined distribution of light illuminates the identification marker when the center of rotation is arranged on the path at a distance from the object under examination, and
   wherein the defined arrangement of the orientation element and the ancillary element is configured to be moved about the center of rotation arranged on the path in an operating state of the device, such that the predefined distribution of light illuminates the identification marker with a predefined light pattern, when the guide axis of the orientation element is oriented in a defined positional relationship in respect of the path.

2. The device of claim 1, wherein the orientation element has a tubular sleeve configured to receive the medical object and guide the medical object along the guide axis.

3. The device of claim 1, wherein the ancillary element has at least one disk-shaped section, and
   wherein the identification marker is arranged on a flat side of the at least one disk-shaped section and/or is integrated into the at least one disk-shaped section.

4. The device of claim 1, wherein the orientation element is movably mounted so as to be forcibly guided by the guide element about at least one axis of rotation that runs through the center of rotation.

5. The device of claim 4, wherein the orientation element is movably mounted so as to be forcibly guided by the guide element about two different axes of rotation that run through the center of rotation.

6. The device of claim 1, wherein the light guiding device is configured to emit the predefined distribution of light containing multiple light fans or light fan beams that do not run parallel to one another and intersect along the path.

7. The device of claim 1, further comprising:
at least one selectively activatable locking element, which, on activation, is configured to:
block the repositioning of the center of rotation; and/or
restrict a movability of the orientation element to a rotation about an axis of rotation that runs through the center of rotation.

8. The device of claim 1, wherein the ancillary element is attached in the defined arrangement to the orientation element and/or is integrated into the orientation element.

9. The device of claim 1, wherein the ancillary element is configured to be repositioned in a longitudinally guided manner in the defined positional relationship in respect of the guide axis from the defined arrangement to a further arrangement, and
wherein the further arrangement of the orientation element and the ancillary element is configured to be moved about the center of rotation, such that the predefined distribution of light illuminates the identification marker with the predefined light pattern, when the guide axis of the orientation element is oriented in the defined positional relationship in respect of the path.

10. The device of claim 9, wherein the orientation element has a tubular sleeve configured to receive the medical object and guide the medical object along the guide axis,
wherein the ancillary element is configured to be introduced at least partially into the tubular sleeve, and
wherein the ancillary element in the defined arrangement is inserted at least partially into the tubular sleeve.

11. The device of claim 10, wherein the ancillary element and/or the orientation element have a positioning device configured to block an introduction of the ancillary element into the tubular sleeve any further than the defined arrangement.

12. The device of claim 11, wherein the ancillary element has a rod-shaped section configured to be introduced at least partially into the tubular sleeve, and
wherein the ancillary element has a further section which forms the positioning device of the ancillary element and mechanically blocks the introduction of the ancillary element into the tubular sleeve any further than the defined arrangement.

13. The device of claim 1, wherein the ancillary element and/or the orientation element have a display device configured to display the defined arrangement of the ancillary element in respect of the orientation element.

14. A system comprising:
a device having an orientation element, a guide element, an ancillary element, and a light guiding device; and
a navigation unit comprising a medical imaging system, a medical navigation system, a medical treatment system, or a combination thereof,
wherein the light guiding device is arranged on the navigation unit and/or is integrated into the navigation unit,
wherein the orientation element is movably mounted so as to be forcibly guided by the guide element about a center of rotation, the center of rotation being repositionable by repositioning the guide element,
wherein the orientation element is configured for a longitudinal guidance of a medical object along a guide axis specified by the orientation element,
wherein the ancillary element has an identification marker,
wherein the ancillary element is configured to be arranged in a defined arrangement in respect of the orientation element, such that the identification marker is arranged in the center of rotation,
wherein the light guiding device is configured to emit a predefined distribution of light that specifies a path,
wherein the predefined distribution of light illuminates the identification marker when the center of rotation is arranged on the path at a distance from an object under examination, and
wherein the defined arrangement of the orientation element and the ancillary element is configured to be moved about the center of rotation arranged on the path in an operating state of the device, such that the predefined distribution of light illuminates the identification marker with a predefined light pattern, when the guide axis of the orientation element is oriented in a defined positional relationship in respect of the path.

15. A method for orienting a medical object by a device, the method comprising:
providing the device having an orientation element, a guide element, an ancillary element, and a light guiding device;
emitting a predefined distribution of light by the light guiding device;
repositioning the guide element such that the predefined distribution of light illuminates an identification marker of the ancillary element, wherein a center of rotation is arranged on a path specified by the predefined distribution of light and at a distance from an object under examination;
repositioning an arrangement of the orientation element and the ancillary element forcibly guided by the guide element about the center of rotation such that the predefined distribution of light illuminates the identification marker with a predefined light pattern, wherein a guide axis of the orientation element is oriented in a defined positional relationship to the path; and
arranging and/or moving the medical object along the guide axis by the orientation element.

16. The method of claim 15, wherein the ancillary element is arranged, prior to the repositioning of the guide element, in a defined arrangement in respect of the orientation element,
wherein the ancillary element, following the arrangement of the center of rotation on the path and prior to the repositioning, is repositioned in a longitudinally guided manner in the defined positional relationship in respect of the guide axis from the defined arrangement to a further arrangement, and
wherein the further arrangement of the orientation element and the ancillary element is moved about the center of rotation, such that the predefined distribution of light illuminates the identification marker with the predefined light pattern, when the guide axis of the orientation element is oriented in the defined positional relationship in respect of the path.

* * * * *

UNITED STATES PATENT AND TRADEMARK OFFICE
CERTIFICATE OF CORRECTION

| | | |
|---|---|---|
| PATENT NO. | : 11,801,069 B1 | Page 1 of 1 |
| APPLICATION NO. | : 18/142772 | |
| DATED | : October 31, 2023 | |
| INVENTOR(S) | : Alois Regensburger | |

It is certified that error appears in the above-identified patent and that said Letters Patent is hereby corrected as shown below:

On the Title Page

Column 1, (72) Inventors:
"ALois Regensburger."

Should be replaced with:
"Alois Regensburger"

Signed and Sealed this
Ninth Day of January, 2024

Katherine Kelly Vidal
*Director of the United States Patent and Trademark Office*